United States Patent
An et al.

(10) Patent No.: US 9,622,664 B2
(45) Date of Patent: Apr. 18, 2017

(54) METHODS AND APPARATUS FOR DETECTING HEART FAILURE DECOMPENSATION EVENT AND STRATIFYING THE RISK OF THE SAME

(71) Applicant: Cardiac Pacemakers, Inc., St. Paul, MN (US)

(72) Inventors: Qi An, Blaine, MN (US); Pramodsingh Hirasingh Thakur, Woodbury, MN (US); Yi Zhang, Plymouth, MN (US); Viktoria A. Averina, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 14 days.

(21) Appl. No.: 14/510,392

(22) Filed: Oct. 9, 2014

(65) Prior Publication Data
US 2015/0126883 A1 May 7, 2015

Related U.S. Application Data

(60) Provisional application No. 61/899,639, filed on Nov. 4, 2013.

(51) Int. Cl.
*A61B 5/02* (2006.01)
*A61B 7/04* (2006.01)
(Continued)

(52) U.S. Cl.
CPC .......... *A61B 5/02028* (2013.01); *A61B 5/686* (2013.01); *A61B 7/045* (2013.01);
(Continued)

(58) Field of Classification Search
None
See application file for complete search history.

(56) References Cited

U.S. PATENT DOCUMENTS 6,334,849 B1 1/2002 Sunagawa
6,477,405 B1 11/2002 Kawaguchi
(Continued)

OTHER PUBLICATIONS

Ahmed, S. Sultan, et al., "Systolic Time Intervals as Measures of the Contractile State of the Left Ventricular Myocardium in Man", Circulation, vol. XLVI, Sep. 1972, 559-571.
(Continued)

*Primary Examiner* — Erica Lee
(74) *Attorney, Agent, or Firm* — Schwegman Lundberg & Woessner, P.A.

(57) ABSTRACT

Devices and methods for detecting heart failure (HF) events or identifying patient at elevated risk of developing future HF events, such as events indicative of HF decompensation status, are described. The devices and methods can detect an HF event or predict HF risk using one or more physiologic sensor signals including an electrogram and a heart sound signal. A medical device can use the physiologic signals to calculate one more signal metrics indicative of systolic function of the heart, including relative timing between first and second signal features selected from signal features generated from the electrogram or the heart sound signals. The medical device can detect an HF event using the signal metrics, or use the signal metrics to calculate a composite risk indicator indicative of the likelihood of the patient later developing an event indicative of worsening of HF.

20 Claims, 8 Drawing Sheets

(51) Int. Cl.
    *A61B 5/00*     (2006.01)
    *A61B 5/0205*   (2006.01)
    *A61B 5/0456*   (2006.01)
    *A61B 5/04*     (2006.01)
(52) U.S. Cl.
    CPC .......... *A61B 5/0006* (2013.01); *A61B 5/0205* (2013.01); *A61B 5/04017* (2013.01); *A61B 5/0456* (2013.01)

(56) References Cited

U.S. PATENT DOCUMENTS

| | | | |
|---|---|---|---|
| 6,643,548 B1 | 11/2003 | Mai et al. | |
| 8,364,263 B2 | 1/2013 | Patangay et al. | |
| 2006/0142667 A1* | 6/2006 | Munk | 600/528 |
| 2008/0103399 A1* | 5/2008 | Patangay | A61B 5/7239 600/508 |
| 2012/0296228 A1* | 11/2012 | Zhang et al. | 600/513 |
| 2013/0339457 A1* | 12/2013 | Freire et al. | 709/206 |

OTHER PUBLICATIONS

Garrard, et al, "The Relationship of Alterations in Systolic Time Intervals to Ejection Fraction in Patients with Cardiac Disease", Circulation, (1970), 455-462.

Weissler, Arnold M, et al., "Systolic Time Intervals in Heart Failure in Man", Circulation, vol. XXXVII, No. 2, (Feb. 1968), 149-159.

* cited by examiner

METHODS AND APPARATUS FOR DETECTING HEART FAILURE DECOMPENSATION EVENT AND STRATIFYING THE RISK OF THE SAME

CLAIM OF PRIORITY

This application claims the benefit of priority under 35 U.S.C. §119(e) of U.S. Provisional Patent Application Ser. No. 61/899,639, filed on Nov. 4, 2013, which is herein incorporated by reference in its entirety.

TECHNICAL FIELD

This document relates generally to medical devices, and more particularly, to systems, devices and methods for detecting and monitoring heart failure decompensation.

BACKGROUND

Congestive heart failure (CHF) is a major health problem and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood.

CHF is usually a chronic condition, but can occur suddenly. It can affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

Overview

Frequent monitoring of CHF patients and timely detection of events indicative of heart failure (HF) decompensation status can help prevent worsening of HF in CHF patients, hence reducing cost associated with HF hospitalization. Additionally, identification of patient at an elevated risk of developing future HF events such as worsening of HF can help ensure timely treatment, thereby improving the prognosis and patient outcome. Identifying and safely managing the patients having risks of future HF events can avoid unnecessary medical intervention and reduce healthcare cost.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory or implantable medical devices can include physiologic sensors which can be configured to sense electrical activity and mechanical function of the heart, or physical or physiological variables associated with the signs or symptoms of worsening of HF. The medical device can optionally deliver therapy such as electrical stimulation pulses to a target area, such as to restore or improve cardiac function or neural function. Some of these devices can provide diagnostic features, such as using transthoracic impedance or other sensor signals. For example, fluid accumulation in the lungs decreases the transthoracic impedance due to the lower resistivity of the fluid than air in the lungs. Fluid accumulation in the lungs can also irritate the pulmonary system and leads to decrease in tidal volume and increase in respiratory rate.

Some ambulatory medical devices can include a physiologic sensor for detecting heart sounds. Heart sounds are associated with mechanical vibrations from activity of a patient's heart and the flow of blood through the heart. Heart sounds recur with each cardiac cycle and are separated and classified according to the activity associated with the vibration. The first heart sound (S1) is associated with the vibrational sound made by the heart during tensing of the mitral valve. The second heart sound (S2) marks the beginning of diastole. The third heart sound (S3) and fourth heart sound (S4) are related to filling pressures of the left ventricle during diastole. Heart sounds are useful indications of proper or improper functioning of a patient's heart. The fluid accumulation in the lungs in HF patients can result in an elevation of ventricular filling pressure, resulting in a louder S3 heart sound.

Worsening of HF status can cause changes in various cardiac functional parameters including systolic timing. For example, HF can significantly reduce the systolic function of the heart, resulting in a prolonged pre-ejection period (PEP). The PEP represents the total duration of the electrical and mechanical events prior to ejection. The PEP can include electrical-mechanical delay between the onset of the ventricular depolarization and the beginning of ventricular contraction, and the isovolumic contraction time during which the left ventricle can contract prior to the opening of the aortic valve. Additionally, HF can cause shortening of left-ventricular ejection time (LVET). The LVET represents the time interval from the opening to the closing of the aortic valve (mechanical systole). Although the systolic timing information such as PEP and LVET can be sensitive to the progression of HF status, confounding factors other than the worsening of HF may also cause changes in systolic timing. Accurate and reliable detection of the changes of these cardiac functional parameters measurement usually require multiple sensors that can simultaneously measure the surface ECG, carotid pulsation or pressure, heart sound, and other physiologic signals, which can be complex and expensive particularly in an ambulatory setting. The present inventors have recognized that there remains a considerable need of systems and methods that can detect target physiologic events indicative of worsening of HF or identify CHF patients with elevated risk of developing future events of worsening of HF with improved accuracy and reliablity, particularly in an ambulatory setting.

Various embodiments described herein can help improve detection of an HF event indicative of worsening of HF, or improve process of identifying patients at elevated risk of developing future HF events. For example, a system can comprise an ambulatory medical device (such as an implantable medical device or a wearable medical device) that can detect an HF event or predict the risk of HF event using one or more signal metrics generated from physiologic signals. The medical device can include a cardiac electrogram sensor circuit configured to sense at least one electrogram and generate one or more electrogram features. A heart sound detector circuit can sense a heart sound signal and generate one or more heart sound features. A target event indicator generator circuit can calculate one more signal metrics indicative of systolic function of the heart, including relative timing between first and second signal features selected from the electrogram features or the heart sound features. The target event indicator generator circuit can further calculate a normalized signal metric using the one or more signal metrics and a normalization factor. The medical device can include a physiologic event detector circuit that can detect an HF event using the signal metrics. Additionally or alternatively, the system can include a risk stratifier circuit that can calculate a composite risk indicator indicative of the likelihood of the patient later developing an event indicative of worsening of HF.

A method can include receiving from a patient at least one electrogram and a physiologic signal indicative of heart sound (HS). The method includes processing the electrogram to generate one or more electrogram features, and processing the heart sound signal to generate one or more heart sound features. The method includes calculating one or more signal metrics indicative of systolic function of the heart. The signal metrics can include indicators of systolic function of the heart, including relative timing between first and second signal features selected from the one or more electrogram features or one or more HS features. One or more normalized signal metrics can be calculated using the one or more signal metrics and a normalization factor. The method can further include using the signal metrics to detect a target physiologic event indicative of worsening of HF using, or to generate a composite risk indicator that can predict the risk of the patient developing a future event indicative of worsening of HF.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting an event indicative of worsening of HF such as an HF decompensation event, and/or for identifying patients with elevated risk of developing future events related to worsening of HF. The HF event detection or HF risk stratification can be performed using the physiologic signals such as sensed from a physiologic sensor associated with an ambulatory medical device such as an implantable cardiac device. The present inventors have recognized that worsening of HF status can cause changes in cardiac systolic timing parameters (such as pre-ejection period, the left-ventricular ejection time, and the systolic timing interval) estimated using ambulatory electrogram sensors and heart sound sensors. Therefore, by analyzing signal metrics derived from the physiologic sensor signals, the present document can provide a method and device to detect the HF event indicative of worsening of HF, or to predict the risk of future HF event, thereby allowing immediate medical attention to the patient.

Figure 1:
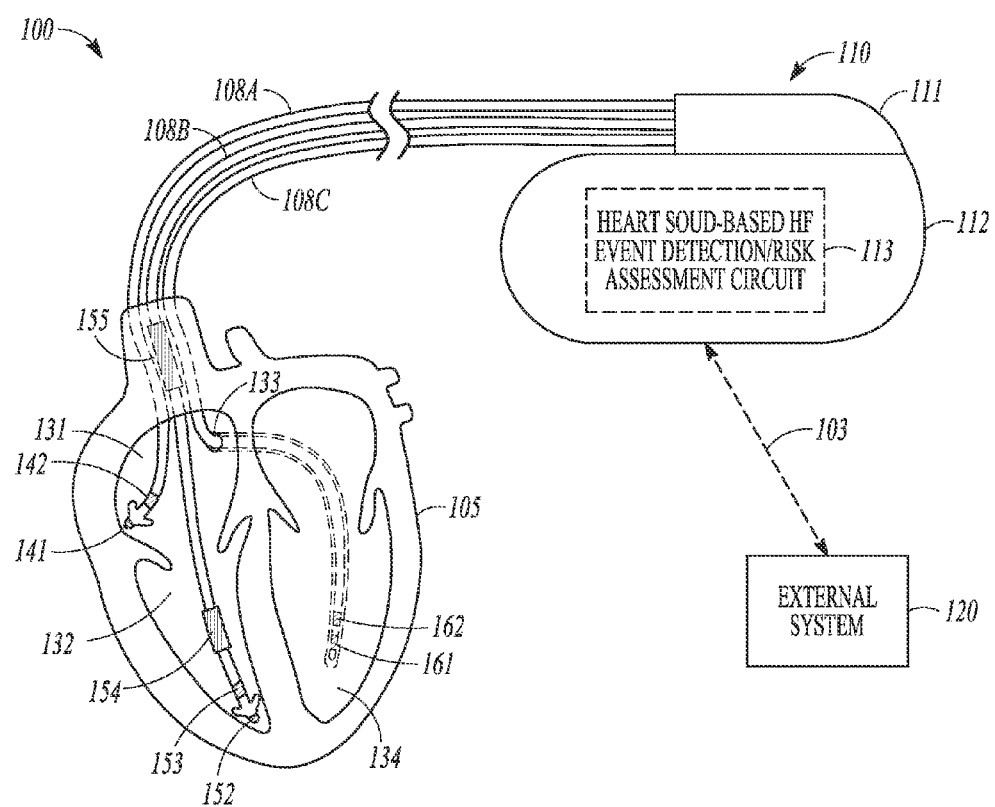
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C'. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of heart rate, heart rate variability, electrocardiograms, intracardiac electrograms, arrhythmias, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a heart sound-based HF event detection/risk assessment circuit 113. The heart sound-based HF event detection/risk assessment circuit 113 can include a physiologic signal receiver circuit, a target event indicator generator circuit, and a physiologic event detector or risk stratifier circuit. The physiologic signal sensor circuit can receive an electrogram indicative of electrical activity of the heart, and generate electrogram features using the electrogram. The electrogram can be sensed using ambulatory physiologic sensors deployed on or within the patient and communicated with the IMD 110, such as electrodes on one or more of the leads 108A-C and the can 112. The physiologic signal receiver circuit can receive heart sound signal such as from one or more ambulatory sensors for sensing a signal indicative of heart sound, and generate one or more heart sound features. The target event indicator generator circuit can generate a signal metric indicative of cardiac systolic timing using the electrogram and the heart sound signals. The physiologic event detector or risk stratifier circuit can generate a trend of the signal metric for use to detect an event of worsening of HF, or to generate a composite risk indicator (CRI) indicative of the likelihood of the patient developing a future event of worsening of HF. The HF decompensation event can include one or more early precursors of an HF decompensation episode, or an event indicative of HF progression such as recovery or worsening of HF status. Examples of heart sound-based HF event detection/risk assessment circuit 113 are described below, such as with reference to FIGS. 2-5.

The external system 120 can allow for programming of the IMD 110 and can receives information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The heart sound-based HF event detection/risk assessment circuit 113 may be implemented at the external system 120, which can be configured to perform HF risk stratification such as using data extracted from the IMD 110 or data stored in a memory within the external system 120. Portions of heart sound-based HF event detection/risk assessment circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
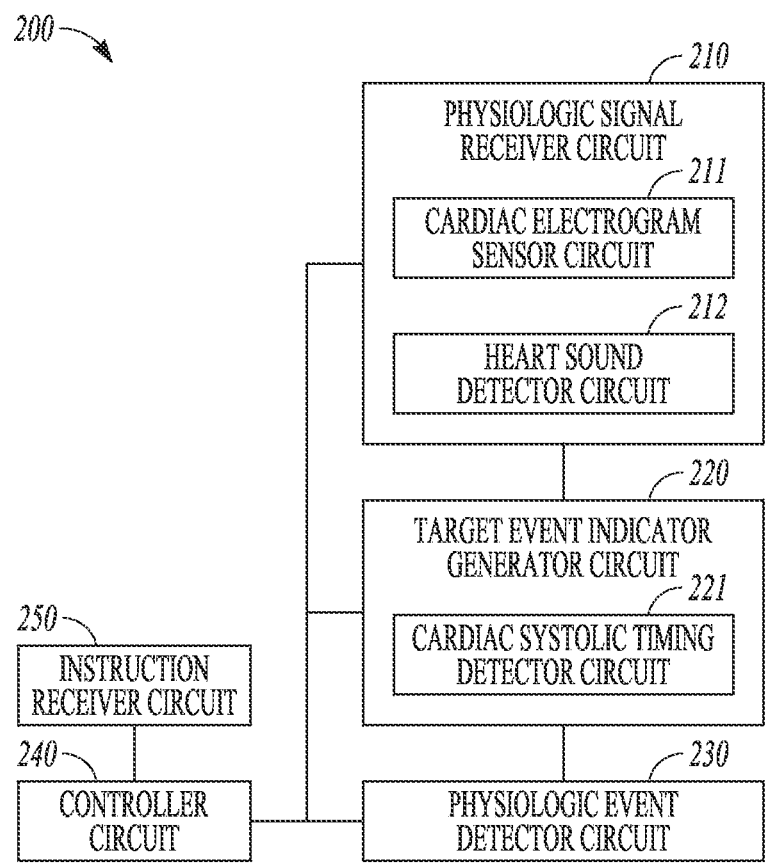
FIG. 2 illustrates an example of a heart sound-based physiologic event detector circuit.

FIG. 2 illustrates an example of a heart sound-based physiologic event detector circuit 200, which can be an embodiment of the heart sound-based HF event detection/risk assessment circuit 113. The heart sound-based physiologic event detector circuit 200 can also be implemented in an external system such as a patient monitor configured for providing the patient's diagnostic information to an end-user. The heart sound-based physiologic event detector circuit 200 can include one or more of a physiologic signal receiver circuit 210, a target event indicator generator circuit 220, a physiologic event detector circuit 230, a controller circuit 240, and an instruction receiver circuit 250.

The physiologic signal receiver circuit 210 can be configured to sense one or more physiological signals that can be indicative of worsening of HF status. The physiologic signals can be sensed using one or more physiologic sensors associated with the patient. Examples of such a physiological signal can include one or more electrograms sensed from the electrodes on one or more of the leads 108A-C or the can 112, heart rate, heart rate variability, electrocardiogram, arrhythmia, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physiologic response to activity, apnea hypopnea index, one or more respiration signals such as a respiration rate signal or a tidal volume signal. In some examples, the physiologic signals can be acquired from a patient and stored in a storage device such as an electronic medical record (EMR) system. The physiologic signal receiver circuit 210 can be coupled to the storage device and retrieve from the storage device one or more physiologic signals in response to a command signal. The command signal can be issued by a system user (e.g., a physician) such as via an input device coupled to the instruction receiver 250, or generated automatically by the system in response to a specified event.

As illustrated in FIG. 2, the physiologic signal receiver circuit 210 can include a plurality of functional components including a cardiac electrogram sensor circuit 211 and a heart sound detector circuit 212. The cardiac electrogram sensor circuit 211 can be configured to sense from a patient at least one electrogram indicative of electrical activity of a heart. The cardiac electrogram sensor circuit 211 can be coupled to one or more electrodes from the implantable leads 108A-C and the can 112 that can sense intracardiac electrograms, or coupled to one or more surface electrodes placed on patient's skin or subcutaneous electrodes disposed under the skin of the patient that can sense electrocardiogram (ECG).

The heart sound detector circuit 212 can be coupled to a heart sound (HS) sensor that can detect the heart sound or other forms of signals as a result of mechanical vibrations of the heart due to cardiac contraction and relaxation. Examples of the HS sensors can include an ambulatory accelerometer or an ambulatory microphone. The HS sensor can be external to the patient or implanted inside the body. In an example, the heart sound sensor can be disposed within an ambulatory medical device such as the IMD 110.

The cardiac electrogram sensor circuit 211 or the heart sound detector circuit 212 can respectively include one or more sub-circuits that can perform signal conditioning (e.g., signal amplification, digitization, or filtering) or feature extraction from the sensed physiological signal. Examples of extracted signal features can include: signal mean, median, or other central tendency measures; a histogram of the signal intensity; one or more signal trends over time; one or more signal morphological descriptors; or signal power spectral density at a specified frequency range. For example, the cardiac electrogram sensor circuit 211 can process the cardiac electrogram and generate one or more electrogram features, including a P wave, Q wave, R wave, T wave, QRS complex, or other components representing depolarization, hyperpolarization, repolarization, or other electrophysiological properties of the myocardium. The heart sound detector circuit 212 can process the HS signal through signal conditioning such as filtering the sensed heart sound signal to a specified frequency range using one or more filters. In an example, the heart sound detector circuit 212 includes a bandpass filter adapted to filter the HS signal to a frequency range of approximately between 5 and 90 Hz. In another example, the heart sound detector circuit 212 includes a bandpass filter adapted to filter the HS signal to a frequency range of approximately between 9 and 90 Hz. The heart sound detector circuit 212 can includes a double or higher-order differentiator configured to calculate a double or higher-order differentiation of the sensed heart sound signal. The heart sound detector circuit 212 can generate one or more heart sound features using the processed HS signal. Examples of the HS features can include timing, amplitude, or morphologic characteristics of at least one of S1, S2 or S3 heart sound. In some examples, the physiologic signal receiver circuit 210 can generate a composite signal parameter using two or more signal features selected from the electrogram features and the HS features.

The target event indicator generator circuit 220 can be configured to generate a plurality of signal metrics from the one or more physiologic signals. The signal metrics can include statistical features (e.g., mean, median, standard deviation, variance, percentile, correlation, covariance, or other statistical value over a specified time segment), morphological features (e.g., peak, trough, slope, area under the curve), or temporal information associated with the physiologic signals (e.g., morning, afternoon, evening, weekday, weekend, seasons). As illustrated in FIG. 2, the target event indicator generator circuit 220 can include a cardiac systolic timing detector circuit 221 configured to generate one or more signal metrics indicative of systolic function of the heart. The signal metrics can include relative timing between first and second signal features selected from electrogram features and HS features. In an example, the first signal feature can be one of the electrogram features and the second signal feature can be one of the HS features. In another example, both the first and second signal features can be two different HS features. Examples of the target event indicator generator circuit 220 are described below, such as with reference to FIG. 4.

The physiologic event detector circuit 230 can receive the signal metrics from the target event indicator generator circuit 220 and detect a physiologic target or condition event using the received signal metrics, such as the signal metrics indicative of the patient's cardiac systolic function. The target event or condition can include a physiologic event preempting a disease or change of disease state, such as an event indicative of HF decompensation, worsening HF, pulmonary edema, or myocardial infarction. The physiologic event detector circuit 230 can be configured to generate a trend of representative values of the signal metrics over a specified time period, and to detect a target physiologic event using at least the trend of representative values of the signal metrics. In an example, the physiologic event detector circuit 230 can determine the trend by calculating a detection index (DI) representing the variation of the values of the signal metrics over time. For example, the DI can be computed as a difference between a first statistical measure of the signal metric computed from a first time window and a second statistical measure of the signal metric computed from a second time window. The first and the second statistical measures can each include a mean, a median, a mode, a percentile, a quartile, or other measures of central tendency of the signal metric values in the respective time window. In an example, the second time window can be longer than the first window, and at least a portion of the second time window precedes the first time window in time. The second statistical measure can represent a baseline value of the signal metric.

The controller circuit 240 can control the operations of the physiologic signal receiver circuit 210, the target event indicator generator circuit 220, the physiologic event detector circuit 230, and the data flow and instructions between these components. The controller circuit 240 can receive external programming input from the instruction receiver circuit 250 to control one or more of the receiving patient status, signal sensing, signal metrics generation, or HF event detection. Examples of the instructions received by instruction receiver 250 may include: selection of electrodes or sensors used for sensing physiologic signals such as the electrograms and the heart sounds, selection of the signal metrics representing the cardiac systolic timing information, or the configuration of the HF event detection. The instruction receiver circuit 250 can include a user interface configured to present programming options to the user and receive user's programming input. In an example, at least a portion of the instruction receiver circuit 250, such as the user interface, can be implemented in the external system 120.

Figure 3:
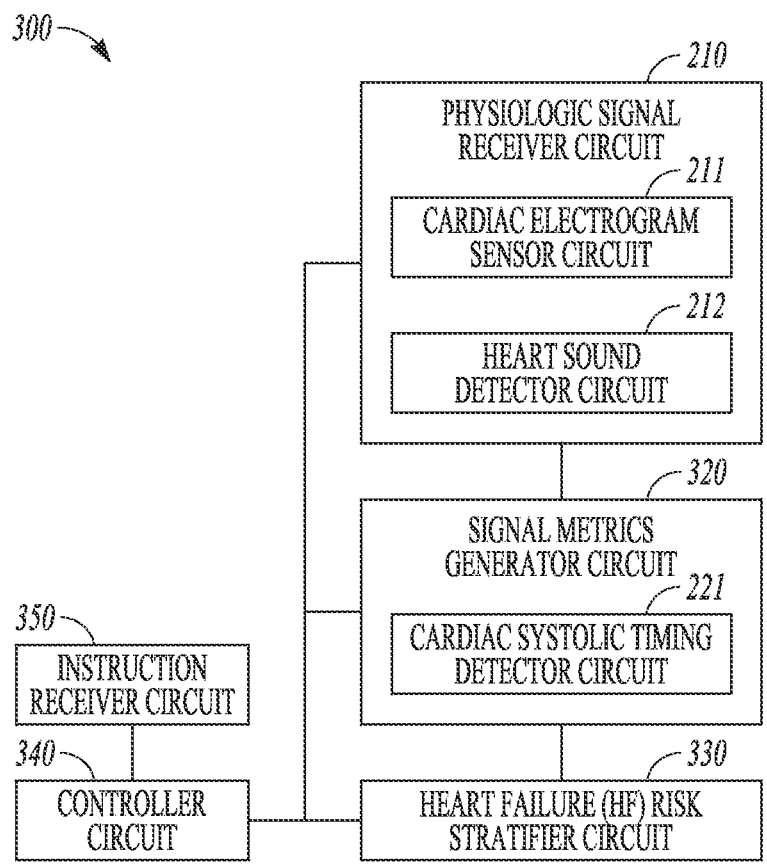
FIG. 3 illustrates an example of a heart sound-based heart failure risk stratifier circuit.

FIG. 3 illustrates an example of a heart sound-based heart failure risk stratifier circuit 300, which can be an embodiment of the heart sound-based HF event detection/risk assessment circuit 113. The heart sound-based heart failure risk stratifier circuit 300 can include one or more of a physiologic signal receiver circuit 210, a signal metric generator circuit 320, a heart failure (HF) risk stratifier circuit 330, a controller circuit 340, and an instruction receiver circuit 350.

As discussed in the heart sound-based physiologic event detector circuit 200 with reference to FIG. 2, the physiologic signal receiver circuit 210 in the heart sound-based heart failure risk stratifier circuit 300 can receive one or more physiologic signals that can be indicative of worsening of HF status. The physiologic signal receiver circuit 210 can include a plurality of functional components including a cardiac electrogram sensor circuit 211 and a heart sound detector circuit 212 that can respectively sense from a physiologic sensor (e.g., the implantable leads 108A-C and the can 112, or implantable accelerometers or microphones), or retrieve from a database (e.g., an EMR system), or receive via an input device receive coupled to the instruction receiver 350, cardiac electrograms or heart sound signals. The cardiac electrogram sensor circuit 211 and the heart sound detector circuit 212 can respectively process the sensed electrogram and the heart sound signal to produce the electrogram features (e.g., R waves or QRS complexes) and HS features (e.g., timing, amplitude, or morphology of S1, S2, S3 heart sounds).

The signal metrics generator circuit 320 can use the one or more physiologic signals to generate a plurality of signal metrics. Examples of the signal metrics can include statistical features (e.g., mean, median, percentile, standard deviation, variance, correlation, covariance, or other statistical value over a specified time segment), morphological features (e.g., peak, trough, slope, area under the curve), or temporal information associated with the physiologic signals (e.g., morning, afternoon, evening, weekday, weekend, seasons). Similar to the target event indicator generator circuit 220 as illustrated in FIG. 2, the signal metrics generator circuit 320 can include a cardiac systolic timing detector circuit 221 configured to generate one or more signal metrics indicative of the cardiac systolic function. The signal metrics can include relative timing between first and second signal features that are generated from one or more physiologic signals, including the electrograms or the heart sound signals. Examples of the signal metrics generator circuit 320 are described below, such as with reference to FIG. 4.

The heart failure (HF) risk stratifier circuit 330 can receive input from the signal metrics generator circuit 320, and calculate a composite risk indicator (CRI) using the one or more signal metrics such as produced by the signal metrics generator circuit 320. The CRI can indicate the likelihood of the patient later developing a target physiologic event such as an event indicating worsening of HF, or HF decompensation in a specified timeframe, such as within approximately 3-6 months, or beyond 6 months. The HF risk stratifier circuit 330 can also be used to identify patients at elevated risk of developing a new or worsening of an existing disease, such as pulmonary edema, pulmonary condition exacerbation such as COPD, asthma and pneumonia, myocardial infarction, dilated cardiomyopathy (DCM), ischemic cardiomyopathy, systolic HF, diastolic HF, valvular disease, renal disease, chronic obstructive pulmonary disease (COPD), peripheral vascular disease, cerebrovascular disease, hepatic disease, diabetes, asthma, anemia, depression, pulmonary hypertension, sleep disordered breathing, hyperlipidemia, among others.

The controller circuit 340 can control the operations of the physiologic signal receiver circuit 210, the signal metrics generator circuit 320, the HF risk stratifier circuit 330, and the data flow and instructions between these components. The controller circuit 340 can receive external programming input from the instruction receiver circuit 350 to control one or more of receiving cardiac electrogram, receiving heart sound signals, generating signal metrics including one or more signal metrics indicative of systolic function of the heart, or calculating a composite risk. Examples of the instructions received by instruction receiver 350 may include: selection of electrodes or sensors used for sensing physiologic signals such as the electrograms and the heart sounds, selection of the signal metrics representing the cardiac systolic timing information, or the parameters used for calculating the composite risk. The instruction receiver circuit 350 can include a user interface configured to present programming options to the user and receive user's programming input. In an example, at least a portion of the instruction receiver circuit 350, such as the user interface, can be implemented in the external system 120.

Figure 4:
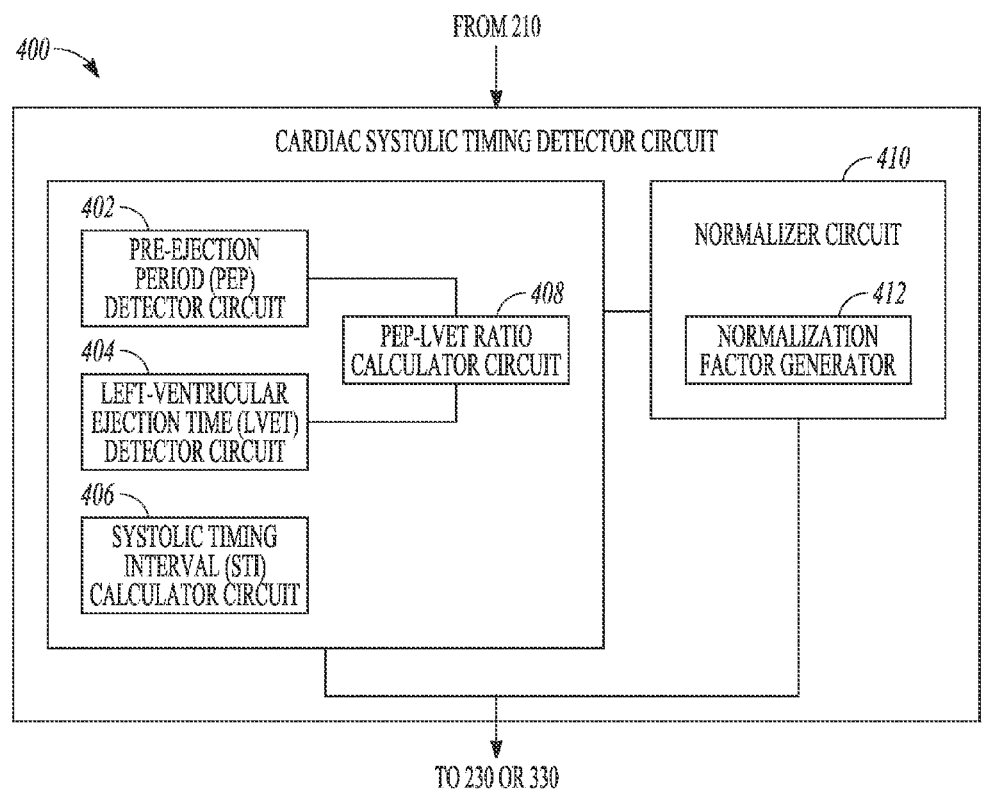
FIG. 4 illustrates an example of a cardiac systolic timing detector circuit.

FIG. 4 illustrates an example of a cardiac systolic timing detector circuit 400, which can be an embodiment of the cardiac systolic timing detector circuit 221 as illustrated in FIGS. 2 and 3. The cardiac systolic timing detector circuit 400 can be configured to generate one or more signal metrics including relative timing between first and second signal features such as between one or more electrogram features or one or more heart sound features. The cardiac systolic timing detector circuit 400 can include one or more of a pre-ejection period (PEP) detector circuit 402, a left-ventricular ejection time (LVET) detector circuit 404, a systolic timing interval (STI) calculator circuit 406, a PEP-LVET ratio calculator circuit 408, and a normalizer circuit 410.

The PEP detector circuit 402 can be configured to determine an electrogram-to-heart sound time interval indicative of the PEP using one or more physiologic signals. The PEP represents the total duration of the electrical and mechanical events prior to ejection. The PEP can include the electrical-mechanical delay which occurs between the onset of the ventricular depolarization and the beginning of ventricular contraction, and the isovolumic contraction time during which the left ventricle can contract prior to the opening of the aortic valve. The PEP detector circuit 402 can calculate the PEP as an interval between timing of a first electrogram feature and timing of a second HS feature. The first electrogram feature can include an onset of a QRS complex, such as Q wave or R wave, on the electrogram such as produced by the cardiac electrogram sensor circuit 211. The second HS feature can include the S1 heart sound such as produced by the heart sound detector circuit 212. The timing of S1 heart sound can indicate the beginning of ventricular ejection. If and when the heart is electrically paced (such as by using an IMD 110 and the associated leads 108A-C or the can 112) such that no spontaneous QRS complex can be detected in the electrogram, the PEP detector circuit 402 can calculate the PEP as an interval from the timing of a ventricular pacing (Vp) signal detected from the electrogram to the timing of the S1 heart sound.

The LVET detector circuit 404 can be configured to determine an intra-heart sound time interval indicative of the LVET. The LVET is the interval of mechanical systole during which blood is ejected into the arterial system. It represents a time interval from the aortic valve opening to aortic valve closure. The LVET can be clinically measured from the beginning of the upstroke to the trough of the incisural notch on the external carotid arterial pulse tracing. The LVET detector circuit 404 can calculate LVET as an interval between timing of a first HS feature indicative of a beginning of ventricular ejection and timing of a second HS feature indicative of an end of ventricular ejection. In an example, the first HS feature can be an S1 heart sound and the second HS feature can be an S2 heart sound. The first and second heart sound features can be produced by the heart sound signal detector circuit 212.

The STI calculator circuit 406 can be configured to determine a systolic timing interval using one or more physiologic signals sensed from physiologic sensors. The STI spans from the electrical excitation of the heart to the closure of the aortic valve, and represents the duration of total electro-mechanical systole. The STI can comprise two major components: the PEP and the LVET, that is, STI≈PEP+LVET. The systolic timing interval (STI) calculator circuit 406 can calculate the STI as an interval between timing of a first electrogram feature indicative of electrical depolarization of the ventricle and timing of a second HS feature indicative of an end of ventricular ejection. In an example, the STI calculator circuit 406 can calculate the STI as an interval between an onset of the QRS complex, such as a Q wave or an R wave, on the electrogram and the S2 heart sound. In some other examples, the STI detector circuit 402 can calculate the STI as a time interval that begins at a ventricular pacing (Vp) signal as detected from the electrogram and ends at the S2 heart sound.

The PEP-LVET ratio calculator circuit 408 can be coupled to the PEP detector circuit 402 and the LVET detector circuit 404, and configured to determine a ratio between the PEP and the LVET, such as PEP/LVET or LVET/PEP. Because in HF patient, particularly those with left ventricular dysfunction, the PEP can be lengthened while the LVET can be shortened, signal metrics like PEP-LVET ratio can be sensitive to the deterioration of the systolic dysfunction in HF patients.

The normalizer circuit 410 can be coupled to one or more of the PEP detector circuit 402, the LVET detector circuit 404, the STI calculator circuit 406, or the PEP-LVET ratio calculator circuit 408. The normalizer circuit 410 can include a normalization factor generator 412 that can generate a normalization factor. The normalizer circuit 410 can use the normalization factor to correct for undesirable impact on the detected PEP, LVET, STI, or PEP/LVET caused by confounding factors including, for example, spontaneous variation of heart rate. Examples of the normalization factor can include physiologic time intervals, such as cardiac cycle, pulse cycle, blood pressure cycle, respiration cycle, time intervals between two heart sound components, or other time intervals measured between two or more physiologic events. In an example, the normalization factor includes a quantity indicative of cardiac cycle, such as an R-R interval (RRI) calculated from the electrogram produced by the cardiac electrogram sensor circuit 211. For example, the LVET can be sensitive to the variation of heart rate such that LVET decreases in response to an increase in heart rate. The normalizer circuit 410 can compute a heart-rate corrected LVET (LVETC) using the normalization factor RRI produced by the normalization factor generator 412. The LVET can be determined as LVET/RRI, or more generally LVET/g(RRI) where g is a linear or nonlinear operator. Compared to LVET, LVETc can be less sensitive to the variation of the heart rate. The LVETc, when used by the physiologic event detector circuit 230 or the HF risk stratifier circuit 330, can more reliably indicate the deterioration of the LV systolic function or the worsening of HF.

Figure 5:
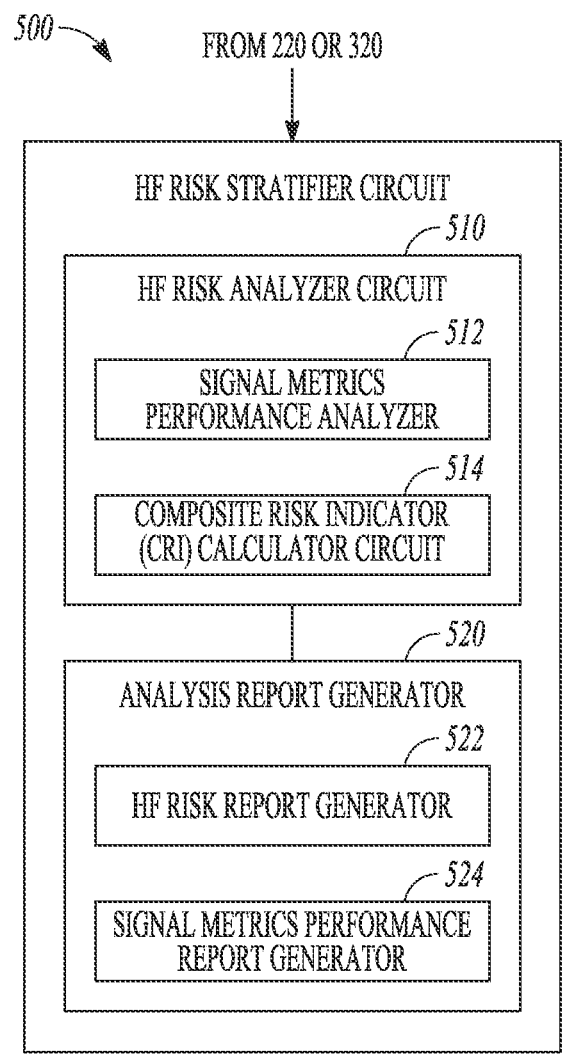
FIG. 5 illustrates an example of an HF risk stratifier circuit.

FIG. 5 illustrates an example of an HF risk stratifier circuit 500, which can be an embodiment of the HF risk stratifier circuit 330. The HF risk stratifier circuit 500 can include an HF risk analyzer circuit 510 and an analysis report generator 520. The HF risk stratifier circuit 500 can receive the signal metrics indicative of cardiac systolic timing or normalized cardiac systolic timing including one or more of the PEP, LVET, STI, or PEP/LVET, analyze the signal metrics, and determine a quantity such as a composite risk indicator (CRI) indicative of a likelihood of the patient developing a future event such as an HF decompensation event.

The HF risk analyzer circuit 510 can include a signal metric performance analyzer 512 and a composite risk indicator (CRI) calculator circuit 514. The signal metrics performance analyzer 512 can be configured to generate for one or more of the signal metrics respective performance measure that indicates reliability or accuracy of predicting a future target physiologic event. Examples of the performance measures can include a predicted hazard ratio, a predicted sensitivity (Se), a predicted specificity (Sp), or a predicted signal quality (Sq), each of which can be determined using population-based statistics. The signal metrics performance analyzer 512 can determine the predicted sensitivity of a signal metric such as PEP/LVET using the relative change of value of the signal metric in response to a physiologic status change associated with the progression of the HF status. In an example, the predicted sensitivity can be determined as a rate of change of the signal metric value from a first time to a second time, where the first and second time can be approximately 1-6 months and 14-28 days respectively prior to the patient's developing a target event such as an HF decompensation event.

The predicted specificity can characterize the accuracy of the signal metric in predicting a confounding event not associated with HF decompensation, such as noise, inference, patient activity, lead fracture, lead revision, change of pacing configuration, or a replacement of the device. The signal metrics performance analyzer 512 can determine the predicted specificity of a signal metric such as the PEP/LVET using the relative change of value of the signal metric from a first time to a second time in response to one or more confounding events. The first and second time can be approximately 1-6 months and 14-28 days respectively prior to patient's developing an HF decompensation event.

The signal metrics performance analyzer 512 can determine the predicted signal quality of a signal metric such as PEP. Examples of the signal quality can include signal strength, signal variability, or signal-to-noise ratio, among others. Signal variability can include range, inter-quartile range, standard deviation, variance, sample variance, or other first-order, second-order, or higher-order statistics representing the degree of variation. For example, in determining the quality of the signal metric of PEP, the signal metrics generator circuit 320 can produce a plurality of measurements of PEP such as from a plurality of cardiac cycles during a specified period of time. The signal metrics performance analyzer 512 can determine the variability of the PEP measurements such as by computing a variance of the PEP measurements. A high signal quality, such as indicated by one or more of high signal-to-noise ratio, high signal strength, or low signal variability, is desirable for identifying patients at an elevated risk of developing future HF events.

The composite risk indicator (CRI) calculator circuit 514 can generate a CRI using one or more signal metrics. In an example, the signal metrics performance analyzer 512 can calculate for each signal metrics ($M_i$) a respective individual risk score ($R_{Mi}$) using a probability model (f) and one or more of the hazard ratio (HR), the predicted sensitivity (Se), the predicted specificity (Sp), and the predicted signal quality (Sq). That is, $R_{Mi}$=f(HR, Se. Sp, Sq). The CRI calculator circuit 514 can compute the CRI using a linear or nonlinear combination of the risk scores ($R_{Mi}$) associated with respective signal metrics. The CRI can be computed as weighted sum of the risk scores, where each risk score can be scaled by a respective weight factor proportional to a performance measure of the signal metric. The CRI can also be determined as a parametric or non-parametric model using the individual risk scores, such as decision trees, neural network, Bayesian network, among other machine learning methods.

The analysis report generator 520 can include an HF risk report generator 522 and a signal metric performance report generator 524. The HF risk report generator 522 can generate a report to inform, warn, or alert a system end-user an elevated risk of a patient developing a future HF event. The report can include the CRI with corresponding timeframe within which the risk is predicted. The report can also include recommended actions such as confirmative testing, diagnosis, or therapy options. The report can include one or more media formats including, for example, a textual or graphical message, a sound, an image, or a combination thereof. In an example, the HF risk report generator 522 can be coupled to the instruction receiver circuit 250 and the report can be presented to the user via an interactive user interface on the instruction receiver circuit 250. The HF risk report generator 402 can be coupled to the external device 120, and be configured to present to the user the risk (e.g., the CRI) of patient developing future HF events via the external device 120.

The signal metrics performance report generator 524 can generate, and present to the user, one or more of a report including the cardiac electrograms such as received by the cardiac electrogram sensor circuit 211, heart sound signals such as received by the heart sound signal detector circuit 212, and the signal metrics representing the cardiac systolic timing information such as generated by the signal metrics generator circuit 320. The signal metrics performance report generator 524 can be coupled to the external device 120 or the instruction receiver circuit 250, and be configured to present the signal metrics information to the user therein. The user input can include confirmation, storage, or other programming instructions to operate on the signal metrics.

Figure 6A:
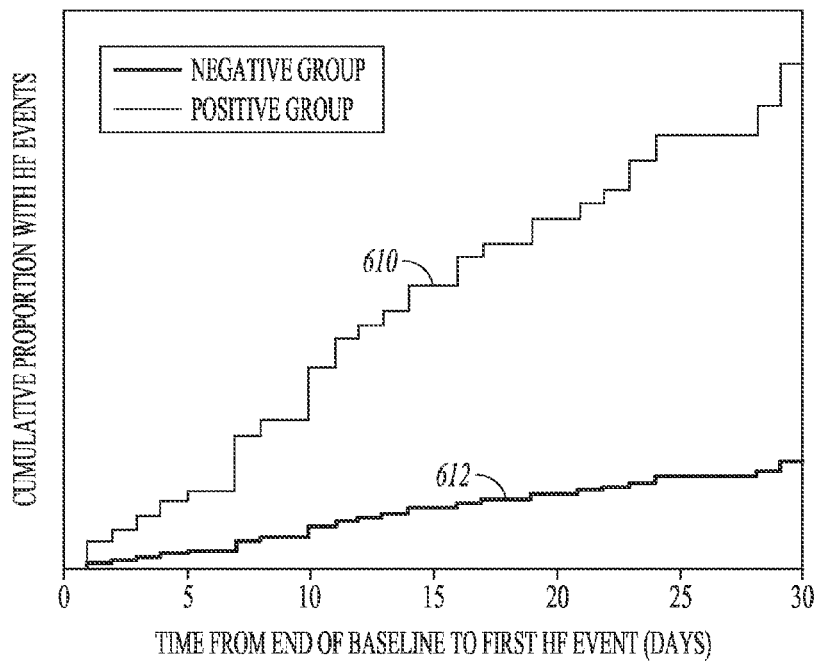
FIGS. 6A-C illustrate exemplary performances of various signal metrics in stratifying risk of patient developing a future target event indicative of HF decompensation.
Figure 6B:
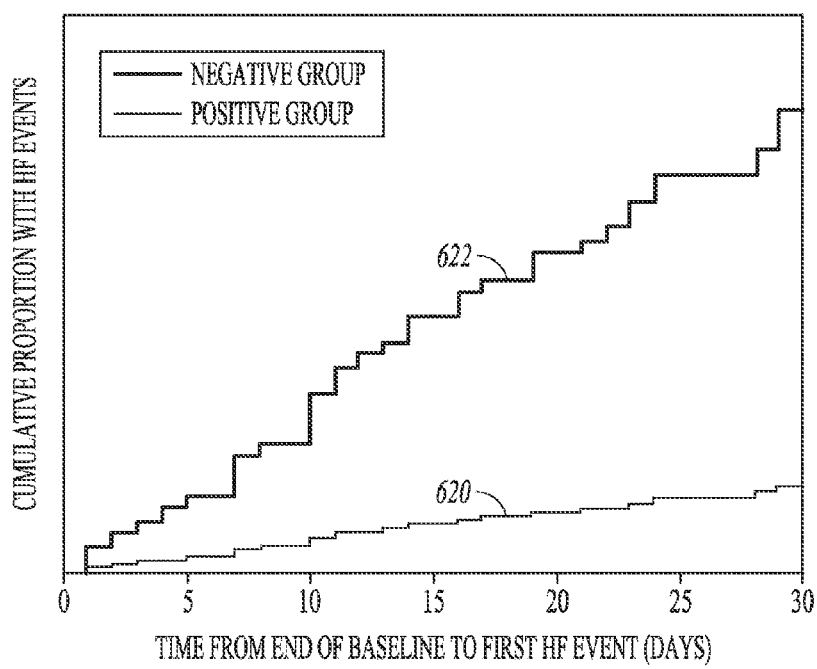
Figure 6C:
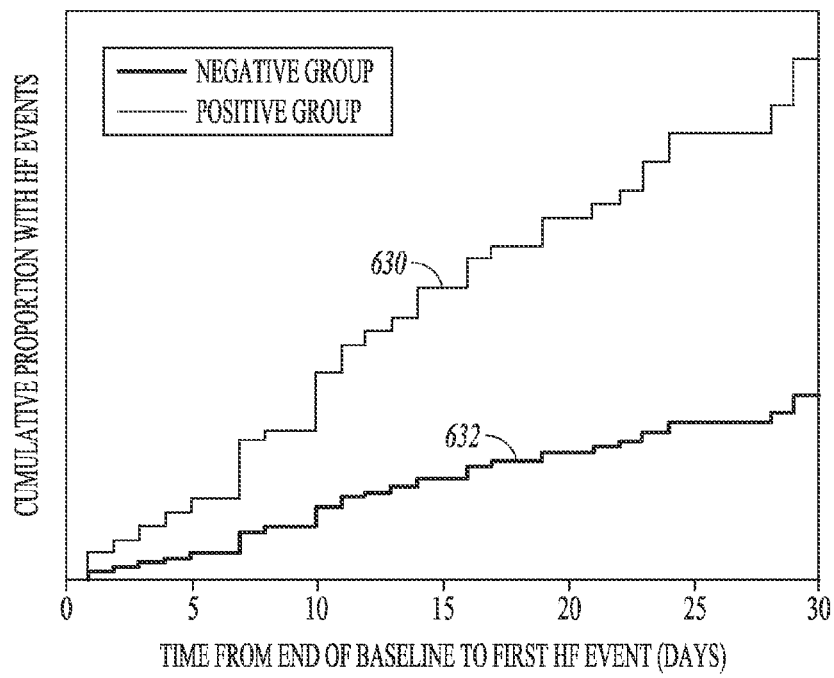

FIGS. 6A-C illustrate examplary performances of various signal metrics in stratifying risk of patient developing a future target event indicative of HF decompensation. Physiologic signals, including the heart sound signals and the cardiac electrograms, can be collected by IMDs implanted from a cohort of patients in one or more analysis sessions during which an HF event is present or absent. The physiological signals can be analyzed using the heart sound-based heart failure risk stratifier circuit 300. The signal metrics, such as those indicative of the PEP, LVET and PEP/LVET, can be generated such as using the cardiac systolic timing detector circuit 400. Each analysis session can be classified into either a positive signal metric group or a negative signal metric group based on a comparison between the values of the signal metrics values and a specified threshold. For example, an analysis session can be classified into a "LVET positive group" if the LVET value is greater than a LVET threshold, or into a "LVET negative group" if the LVET value is no greater than a LVET threshold. Data from each group can be fit into a respective regression model that provides a prediction of the risk (such as a probability or likelihood measure) of an HF event occurring at a specified time. In the examples illustrated in FIGS. 6A-C, risk prediction can be performed using a Cox regression model which provides a survival curve, or an event curve, that depicts cumulative proportion of the HF decompensation events (on the y-axis) within a specified time-to-event interval (on the x-axis) such as number of days elapsed from a baseline reference event to the occurrence of the first HF decompensation event.

FIG. 6A illustrates the performance of a risk stratifier that uses heart-rate corrected, heart-sound based signal metric indicative of PEP (HS-PEP). The HS-PEP can be determined using the PEP detector circuit 402, and normalized by the normalizer circuit 410 such as using a normalization factor equaling the R-R interval (RRI). Values of HS-PEP can be compared to a threshold and classified into either a HS-PEP positive group if HS-PEP is substantially prolonged (such as greater than a specified threshold), or a HS-PEP negative group if HS-PEP is not substantially prolonged (such as no greater than the specified threshold). As illustrated in FIG. 6A, event curve for the HS-PEP positive group 610 has a steeper slope than the event curve for the HS-PEP negative group 620, indicating that the HS-PEP positive group has a faster increase in the accumulated HF decompensation events than the HS-PEP negative group as HF status progresses. A relative risk of having a future HF decompensation event associated with an elevated HS-PEP, such as a hazard ratio, can be computed. In the example of FIG. 6A, a hazard ratio is approximately 4-5, suggesting that patients with substantially prolonged HS-PEP can be 4-5 times more likely to develop a future HF decompensation event than the patients whose HS-PEPs are not substantially prolonged.

FIG. 6B illustrates the performance of a risk stratifier that uses a heart-sound based signal metric indicative of LVET (HS-LVET). The HS-LVET can be determined using the LVET detector circuit 404. Because LVET may not be very sensitivity to the confounding factors like spontaneous fluctuation of heart rate, in the example illustrated in FIG. 6B, the normalization factor can be set to a default value of one in the normalization factor generator 412. This is equivalent to no normalization of the HS-LVET. Values of HS-LVET can be compared to a threshold and classified into either a HS-LVET negative group if HS-LVET is substantially shortened (such as less than a specified threshold), or a HS-LVET positive group if HS-PEP is not substantially shortened (such as no less than the specified threshold). As illustrated in FIG. 6B, the event curve for the HS-LVET negative group 622 has a steeper slope than the event curve for the HS-LVET positive group 620. In this example, a Cox regression analysis yields a hazard ratio of approximately 3-4, suggesting that the patients with substantially shortened HS-LVET are 3-4 times more likely to develop a future HF decompensation event than the patients with normal HS-LVET.

FIG. 6C illustrates the performance of a risk stratifier that uses a heart-sound based signal metric indicative of the PEP/LVET (HS-PEP/LVET). The HS-PEP/LVET can be determined using the PEP-LVET ratio calculator circuit 408. In this example, the HS-PEP/LVET can be computed from a filtered heart sound signal generated by passing the HS signal through a double differentiator such as implemented in the heart sound detector circuit 212. Values of HS-PEP/LVET can be compared to a threshold and classified into either a HS-PEP/LVET positive group if HS-PEP/LVET is substantially prolonged (such as greater than a specified threshold), or a HS-PEP/LVET negative group if HS-PEP/LVET is not substantially prolonged (such as no greater than the specified threshold). As illustrated in FIG. 6C, the event curve for the HS-PEP/LVET positive group 630 has a steeper slope than the event curve for the HS-PEP/LVET negative group 632. A Cox regression analysis yields a hazard ratio of approximately 5-6, suggesting that the patients with substantially prolonged HS-PEP/LVET are 5-6 times more likely to develop a future HF decompensation event than the patients whose HS-PEP/LVETs are not substantially prolonged.

Figure 7:
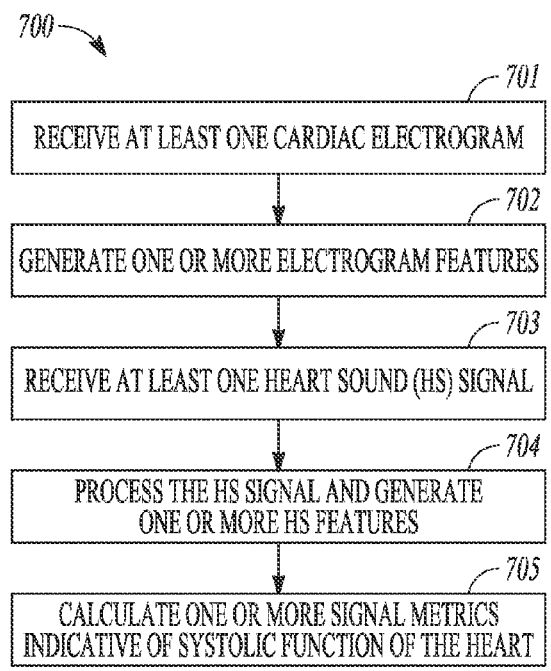
FIG. 7 illustrates an example of a method for evaluating cardiac systolic function of a patient.

FIG. 7 illustrates an example of a method 700 for evaluating cardiac systolic function of a patient. The method 700 can be implemented and operate in an ambulatory medical device or in a remote patient management system. In an example, the method 700 can be performed by the heart sound-based HF event detection/risk assessment circuit 113 implemented in the IMD 110, or the external device 120 which can be in communication with the IMD 110.

At 701, at least one cardiac electrogram can be received from a patient. The cardiac electrogram can include intracardiac electrogram sensed using physiologic sensors such as one or more electrodes on one or more of transvenous leads 108A-C coupled to an implantable medical device (IMD) and the can 112 of the IMD, surface electrocardiogram (ECG) sensed using one or more surface electrodes placed on patient's skin, subcutaneous electrogram sensed using subcutaneous electrodes disposed under the skin of the patient, or any other cardiac signals indicative of electrical activity of a heart. Alternatively or additionally, the cardiac electrogram of a patient can be stored in a storage device such as an electronic medical record (EMR) system, and can be retrieved from the storage device upon receiving a command such as issued by an end-user. The received cardiac electrogram can be analyzed at 702 to generate one or more electrogram features including a P wave, R wave, T wave, QRS complex, or other components representing depolarization, hyperpolarization, repolarization, or other electrophysiologic properties of the myocardium.

At 703, at least one physiologic signal indicative of heart sound (HS) of the patient can be received. The signal indicative of HS can be sensed using a HS sensor that can detect heart sound wave or other forms of signals such as vibrations of the chest wall resulting from cardiac mechanical contraction and relaxation. Examples of the HS sensors can include an ambulatory accelerometer or an ambulatory microphone. The physiologic signals indicative of HS can be stored in a storage device such as an EMR system, and can be retrieved from the storage device upon receiving a command such as issued by an end-user.

The received HS signal can be processed at 704, including signal amplification, analog to digital conversions, signal filtering, or other signal conditioning processes. The received HS signal can be filtered to a specified frequency range using one or more filters, including a bandpass filter characterized by specified cutoff frequencies, bandwidth, passband gain, stopband attenuation, among other parameters. For example, the bandpass filter can have a passband of approximately 5 to 90 Hz. In another example, the bandpass filter has a passband of approximately 9 to 90 Hz. The HS signal can be processed using a double or higher-order differentiator configured to calculate a double or higher-order differentiation of the HS signal. From the processed HS signal, one or more HS features can be generated, including timing with respect with respect to a specified reference event, amplitude, or morphological features of S1, S2 or S3 heart sounds.

At 705, one or more signal metrics indicative of systolic function of the heart can be calculated such as using the one or more electrogram features produced at 702, the one or more HS features produced at 704, or both the electrogram features and the HS features. The signal metrics can include relative timing between first and second signal features selected from the one or more electrogram features and the one or more HS features. In an example, the signal metrics can include a time interval indicative of the pre-ejection period (PEP), such as an interval between one of the Q wave or an R wave sensed from an electrogram and the S1 hear sound sensed from the HS signal. In another example, the signal metrics can include a time interval indicative of the left ventricular ejection time (LVET), such as an interval between the S1 and S2 heart sounds. In yet another example, the signal metrics can include a ratio between the time interval indicative of the PEP and the time interval indicative of the LVET. The signal metrics can be normalized using a normalization factor to correct for undesirable impact on the detected PEP, LVET, STI, or PEP/LVET caused by confounding factors including, for example, spontaneous variation of heart rate. Examples of the normalization factor can include physiologic time intervals, such as cardiac cycle, pulse cycle, blood pressure cycle, respiration cycle, or other time intervals measured between two or more physiologic events. In an example, the normalization factor includes a quantity indicative of cardiac cycle, such as an R-R interval (RRI). The signal metrics can be presented to the end-user for monitoring the patient health status or disease progress such as worsening of HF. The signal metrics can also be used for detecting the presence of a target physiologic event such as an indication of an HF decompensation event, for predicting the future risk of developing a target physiologic event, or for titrating medical or device therapies to the patient such as by adjusting the dosage or parameters associated with the electrical stimulation.

Figure 8:
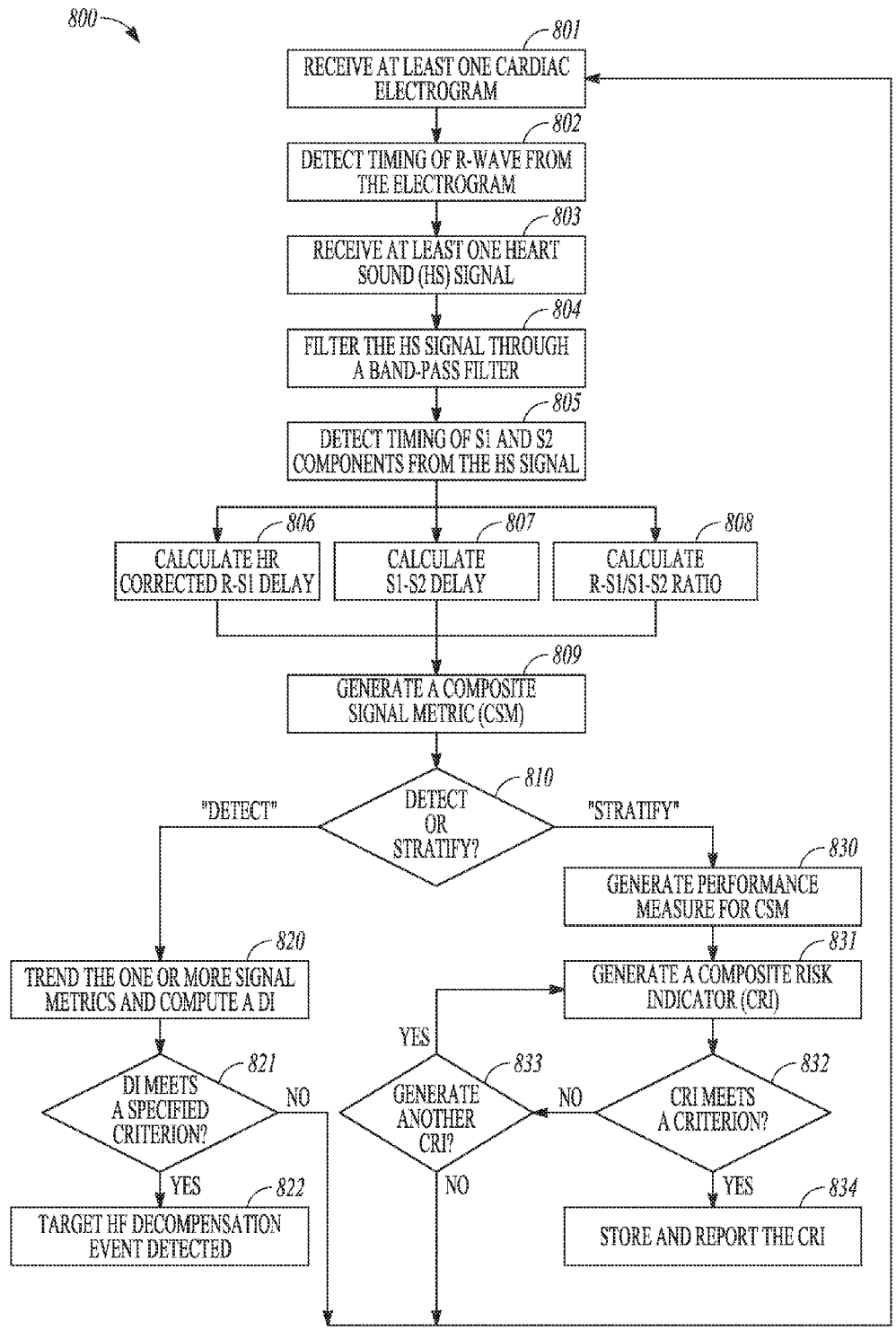
FIG. 8 illustrates an example of a method for detecting an HF event or providing a risk stratification of a future HF event.

FIG. 8 illustrates an example of a method 800 for detecting an HF event indicative of HF decompensation or providing a risk stratification of a future HF event. The method 800 can be an embodiment of the method 700 for evaluating cardiac systolic function of a patient, further including method for detecting a present HF event or predicting a future HF event using the cardiac systolic function evaluation. In an example, the method 700 can be performed by the HS-based HF event detection/risk stratification circuit 113.

At 801, at least one cardiac electrogram can be received from a patient. The cardiac electrogram can include intracardiac electrogram, surface electrocardiogram (ECG), subcutaneous electrogram, or any other cardiac signals indicative of electrical activity of a heart. The cardiac electrogram can be sensed using a physiologic sensor or a plurality of electrodes attached to or implanted within the patient body. The cardiac electrogram can be retrieved from a database such as residing in an electrical medical record (EMR) system that retrievably stores patient's electrograms. The received cardiac electrogram can be analyzed at 802 to generate one or more electrogram features including a P wave, R wave, T wave, QRS complex, or other components representing depolarization, hyperpolarization, repolarization, or other electrophysiologic properties of the myocardium.

At 803, a signal indicative of heart sound (HS) can be sensed such as using an implantable accelerometer, microphone, or other heart sound sensors. The HS signal can be sensed simultaneously with the cardiac electrogram. The HS signal can also be received from a physiologic signal database such as residing in an EMR system, and the received HS signal can be in synchronization with the cardiac electrogram retrievably stored in the physiologic signal database. The received HS signal can be filtered at 804 through one or more filters, such as a bandpass filter with a passband of 5 to 90 Hz. In another example, the bandpass filter has a passband of approximately 9 to 90 Hz. The HS signal can be processed at 804 using a double or higher-order differentiator configured to calculate a double or higher-order differentiation of the HS signal.

At 805, HS features such as S1 and S2 heart sounds can be detected from the processed HS signal. Strength of S1 or S2, such as the amplitude in time, frequency, or other transformation domain, or signal energy within respective S or S2 detection time window, can be computed. The strength of S1 or S2 can each be compared to a respective threshold to determine the presence of the S1 and S2 heart sounds. The timing of S1 and S2 with respect to a fiducial point, such as the detected R wave or QRS complex immediately preceding the detected S1 and S2 heart sound, can also be determined at 805.

One or more signal metrics indicative of systolic function of the heart can then be calculated at 806, 807 and 808. At 806, a heart rate corrected R wave to S1 heart sound (R-S1) delay can be computed. R-S1 delay can be indicative of the pre-ejection period (PEP). The R-S1 delay within each cardiac cycle can be normalized by the R-R interval of the present cardiac cycle to lessen the confounding effect of heart rate on the R-S1 delay, which can reduce the false positive detections of HF decompensation event. Additionally or alternatively, at 807, a S1-S2 delay can be computed using the detected timing of S1 and S2 heart sounds. The S1-S2 delay can be indicative of the left ventricular ejection time (LVET). Additionally or alternatively, at 808, an R-S1/S-S2 ratio can be computed using the R-S1 interval and the S1-S2 interval from the same cardiac cycle. The R-S1/S1-S2 ratio is indicative of PEP/LVET ratio and can be used to evaluate the systolic function of the heart.

One or more of a representative heart-rated corrected R-S1 delay, a representative S1-S2 delay, or a representative R-S1/S1-S2 ratio can be generated for used in HF event detection or HF risk stratification. The representative signal metrics (such as the representative heart-rate corrected R-S1 delay) can be calculated as an average, a median, or other central tendency measure across signal metric values measured over a plurality of cardiac cycles or a specified time period.

At 809, a composite signal metric (CSM) can be generated. The composite signal metric can be any one of the signal metrics calculated at 806 through 808, including R-S1 delay, S1-S2 delay, R-S1/S1-S2 ratio, any combination of these signal metrics, or any combination of these signal metrics with other signal metrics computed from physiologic signals including heart rate, heart rate variability, electrocardiogram, intracardiac electrogram, arrhythmia, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiologic response to activity, posture, respiration, body weight, or body temperature.

At 810, a choice is made, such as by an end-user through a programming device, to select between using the CSM to detect a presence of an event indicative of HF decompensation and using the CSM to stratify patient's risk of developing a future event indicative of HF decompensation. If the choice is to "detect" HF decompensation, then at 820, a trend can be generated using the one or more signal metrics, such as the R-S1 delay, the S1-S2 delay, the R-S1/S1-S2 ratio. The trend of a signal metric can indicate variation of the signal metric value over time. The trend can be quantitatively represented by a detection index (DI). The DI can be calculated as a difference between a first statistical measure of the signal metric computed from a first time window and a second statistical measure of the signal metric computed from a second time window. The first and second statistical measures can each include a mean, a median, a mode, a percentile, a quartile, or other measures of central tendency of the signal metric values in the respective time window. In an example, the second time window can be longer than the first window, and at least a portion of the second time window precedes the first time window in time.

The second statistical measure can be indicative of a baseline value of the signal metric. For example, a DI can be calculated as the difference between an average R-S1 delay in the first window (R-S1$_{W1}$) and an average R-S1 delay in the second window representing the baseline R-S1(R-S1$_{baseline}$), that is, DI=R-S1$_{W1}$-R-S1$_{baseline}$. The DI can also be calculated as a rate of change from the second statistical measure to the first statistical measure. For example, the DI for the HR-corrected R-S1 delay can be determined as DI=(R-S1$_{W1}$-R-S1$_{Baseline}$)(T$_{W1}$-T$_{baseline}$), where T$_{Baseline}$ and T$_{W1}$ are the representative time for the first and second time window, respectively.

A decision is made at 821 as to whether the DI meets a specified criterion, such as exceeding a specified threshold. If the DI meets the criterion, then a target HF decompensation event is deemed detected at 822. For example, if the increase or the rate of increase in HR-corrected R-S1 exceeds a specified threshold, or the shortening or rate of shortening of S1-S2 delay exceeds a specified threshold, or the increase or the rate of increase in R-S1/S1-S2 exceeds a specified threshold, an HF decompensation event is deeded detected at 822. However, if the DI does not meet the criterion at 821, then the patient monitoring can be continued with receiving the physiological signals such as the cardiac electrogram at 801.

If at 810 a choice is made to "stratify" the patient's risk, then at 830 a performance measure can be computed for the composite signal metric. The performance measure of a signal metric can indicate reliability or accuracy of predicting a risk of the target event such as a future HF decompensation event using the signal metric. Examples of the performance measures can include a predicted hazard ratio, a predicted sensitivity, a predicted specificity, or a predicted signal quality determined using population-based statistics. In an example, the predicted sensitivity can be determined as the rate of change of the signal metric value from a first time to a second time, where the first and second time can be approximately 1-6 months and 14-28 days respectively prior to patient's developing an HF decompensation event. The predicted specificity can characterize the accuracy of the signal metric in predicting a confounding event not associated with HF decompensation, such as noise, inference, patient activity, lead fracture, lead revision, change of pacing configuration, or a replacement of the device. The predicted signal quality can include signal strength, signal variability, or signal-to-noise ratio, among others. Signal variability can include range, inter-quartile range, standard deviation, variance, sample variance, or other first-order, second-order, or higher-order statistics representing the degree of variation. A high signal quality, such as indicated by one or more of a high signal-to-noise ratio, high signal strength, or a low signal variability, is desirable for identifying patients at the elevated risk of developing future HF events.

At 831, a composite risk indicator (CRI) can be generated. The CRI can be a quantity that indicates the probability or likelihood of the patient developing a future event indicative of worsening of HF, such as excessive intrathoracic fluid accumulation, increased heart sounds, increased heart rate, increased respiratory rate, decreased tidal volume, increase in pressure, reduction in activity, or other events indicative of HF decompensation status. The CRI can be computed using one or more signal metrics indicative of cardiac systolic timing information. A respective individual risk score (R$_{Mi}$) can be calculated for each signal metric (Mi) using a probability model (f) and one or more of the predicted hazard ratio (HR), the predicted sensitivity (Se), the predicted specificity (Sp), and the predicted signal quality (Sq). That is, R$_{Mi}$=f(HR, Se, Sp, Sq). The CRI can be computed as a linear or nonlinear combination of the risk scores associated with respective signal metrics. The CRI can be computed as weighted sum of the risk scores, where each risk score can be scaled by a respective weight factor proportional to a performance measure of the signal metric. The CRI can also be determined as a parametric or non-parametric model using the individual risk scores such as decision trees, neural network, Bayesian network, among other machine learning methods.

At 832, the CRI is checked against a specified criterion, such as a reference or threshold value, to determine the risk of the patient developing a future HF event. The reference measure can be computed from data from a patient population. The reference measure computed from such a population can indicate an "average" patient's risk of developing future HF events. The reference measures can include: the mean, median, a range, or other central tendency of the risk across the patient population; variance, standard deviation, or other second or higher order statistical measures across the patient population; histogram, statistical distribution, or the parametric or non-parametric model representing the histogram or statistical distributions.

The comparison can include computing a dissimilarity between the CRI and the reference. Examples of the dissimilarity can include a difference, a ratio, a percentile change, or other relative change. The dissimilarity can be computed as multi-dimensional distance using the statistical distribution of the reference measure. The dissimilarity can be compared to one or more thresholds such that the CRI can be categorized to two or more categorical risk levels indicating elevated risk of the patient later developing the HF event. For example, the categorical levels can include "high risk", "medium risk", or "low risk." A higher degree of dissimilarity between the CRI and the reference can indicate a higher risk of the patient developing HF events in the future than an average patient with the similar chronic conditions.

If at 832 the CRI meets the specified criterion such as the CRI value being categorized as "medium risk" or "high risk" level, then at 834 a report is generated to inform, warn, or alert the user the elevated risk of patient's developing a future HF event. The report can include any or all of the information of the signal metrics selected for analysis, the CRI, the categorical classifications of CRI, one or more composite risk indices with corresponding timeframe within which the risk is predicted. The report can also include recommendations for intervention, further testing, or treatment options for the patient. The report can be in a form of a textual or graphical message, a sound, an image, or any combination thereof.

If the CRI does not meet the specified criterion, then at 833 a decision is made as to whether a new CRI is to be computed such as using additional signal metrics. The decision at 833 can be received from an end-user such as using a programming device, or automatically executed in response to the CRI failing to meet the criterion by a narrow margin. If additional signal metrics are decided to be used at 833, then a new CRI can be generated at 831; otherwise, the patient is deemed at low risk of developing future HF event, and no preventive action is deemed necessary. The patient monitoring can be continued with receiving the physiological signals such as the cardiac electrogram at 801.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   an ambulatory medical device (AMD) including:
      a cardiac electrogram sensor circuit configured to sense from a patient at least one electrogram and to generate one or more electrogram features using the sensed electrogram, the electrogram indicative of electrical activity of a heart of the patient;
      a heart sound detector circuit configured to sense from the patient a vibratory or acoustic heart sound (HS) signal and to generate one or more HS features using the sensed HS signal;
      a target event indicator generator circuit configured to:
         calculate a first normalized signal metric including a first relative timing normalized by a normalization factor, the first relative timing measured between a first pair of signal features selected from the one or more electrogram features or the one or more HS features; and
         calculate a second unnormalized signal metric including a second relative timing measured between a different second pair of signal features selected from the one or more electrogram features or the one or more HS features signal metric; and
      a physiologic event detector circuit coupled to the target event indicator generator circuit, the physiologic event detector circuit configured to detect a target physiologic event using a combination of at least the first normalized signal metric and the second unnormalized signal metric.

2. The system of claim 1, wherein the physiologic event detector circuit is configured to detect worsening of heart failure.

3. The system of claim 1, wherein the target event indicator generator circuit is configured to calculate the first normalized signal metric including an electrogram-to-heart sound time interval indicative of a pre-ejection period (PEP), the electrogram-to-heart sound time interval including a delay from a first electrogram feature to a second HS feature.

4. The system of claim 1, wherein the target event indicator generator circuit is configured to calculate the second unnormalized signal metric including an intra-heart sound time interval indicative of a left-ventricular ejection time (LVET), the intra-heart sound time interval including an interval between a first heart sound S1 and a second heart sound S2 of the sensed HS signal.

5. The system of claim 1, wherein at least one of the first normalized or second unnormalized signal metric includes a ratio between a first time interval indicative of the PEP and a second time interval indicative of the LVET.

6. The system of claim 1, wherein the target event indicator generator circuit is configured to generate the normalization factor including a representative value of a physiologic time interval.

7. The system of claim 1, comprising a heart sound sensor coupled to the heart sound detector circuit, wherein the HS sensor is adapted to sense from the patient a physiologic signal indicative of heart sound.

8. The system of claim 1, wherein the heart sound detector circuit includes at least one filter circuit configured to filter the sensed heart sound signal to a specified frequency range, the heart sound detector configured to generate the HS features including timing of at least one of a first heart sound S1, a second heart sound S2, or a third heart sound S3 using the filtered HS signal.

9. The system of claim 8, wherein the filter circuit includes a double differentiator circuit configured to calculate a double differentiation of the sensed HS signal.

10. The system of claim 8, wherein the filter circuit includes a band-pass filter.

11. The system of claim 10, wherein the band-pass filter has cutoff frequencies of 5 Hz and 90 Hz.

12. The system of claim 1, wherein the physiologic event detector circuit is further configured to:
generate, for the one or more signal metrics, respective predicted performance measures including one or more of a predicted sensitivity, a predicted specificity, or a predicted signal quality; and
detect the target physiologic event further using the respective predicted performance measures.

13. A system, comprising:
a signal analyzer circuit, including:
a cardiac electrogram sensor circuit configured to sense at least one electrogram of a heart of a patient and to generate one or more electrogram features using the sensed electrogram, the electrogram indicative of electrical activity of the heart;
a heart sound (HS) signal detector circuit configured to sense a HS signal of the patient and to generate one or more HS features using the sensed HS signal; and
a signal metric generator circuit configured to:
calculate a first normalized signal metric including a first relative timing normalized by a normalization factor, the first relative timing measured between a first pair of signal features selected from the one or more electrogram features or the one or more HS features; and
calculate a second unnormalized signal metric including a second relative timing measured between a different second pair of signal features selected from the one or more electrogram features or the one or more HS features a normalized first signal metric using the first signal metric and a normalization factor; and
a risk stratifier circuit configured to calculate a composite risk indicator using a combination of at least the first normalized signal metric and the second unnormalized signal metric, the composite risk indicator indicative of the likelihood of the patient developing a future target physiologic event.

14. The system of claim 13, wherein:
the cardiac electrogram sensor circuit is configured to generate the one or more electrogram features including timing of an R wave on the sensed electrogram;
the HS signal detector circuit is configured to generate the one or more HS features including relative timing of a first heart sound S1, a second heart sound S2, or a third heart sound S3 with respect to the timing of the R wave; and
the signal metric generator circuit is configured to calculate the first normalized signal metric using at least a first time interval indicative of the pre-ejection period (PEP) and to calculate the second unnormalized signal metric using at least a second time interval indicative of the left ventricular ejection time (LVET), the first time interval including an interval between the R wave and the S1 heart sound, the second time interval including an interval between the S1 and S2 heart sounds.

15. The system of claim 13, wherein the risk stratifier circuit is configured to calculate for the first normalized signal metric and the second unnormalized signal metric respective individual risk scores, and to calculate the composite risk indicator using a linear or nonlinear combination of the individual risk scores for the first normalized signal metric and the second unnormalized signal metric.

16. A method, comprising:
receiving from a patient at least one electrogram indicative of electrical activity of a heart of the patient;
generating one or more electrogram features using the sensed electrogram;
receiving from the patient a physiologic signal indicative of heart sound (HS);
processing the sensed physiologic signal including filtering the sensed physiologic signal using a filter with specified frequency response;
generating one or more HS features using the processed physiologic signal;
calculating a first normalized signal metric including a first relative timing normalized by a normalization factor, the first relative timing measured between a first pair of signal features selected from the one or more electrogram features or the one or more HS features;
calculate a second unnormalized signal metric including a second relative timing measured between a different second pair of signal features selected from the one or more electrogram features or the one or more HS features signal metric; and
generating a composite signal metric using a combination of at least the first normalized signal metric and the second unnormalized signal metric.

17. The method of claim 16, comprising detecting a target physiologic event indicative of worsening of heart failure using the composite signal metric.

18. The method of claim 16, comprising generating a composite risk indicator using a combination of at least the first normalized signal metric and the second unnormalized signal metric, the composite risk indicator indicative of the likelihood of the patient developing a future event indicative of worsening of heart failure.

19. The method of claim 16, wherein processing the sensed physiologic signal includes calculating a double differentiation of the sensed acceleration signal.

20. The method of claim 16, wherein:
generating the one or more electrogram features includes generating timing of an R wave on the sensed electrogram;
generating the one or more HS features includes generating timing of one or more of a first heart sound S1, a second heart sound S2, or a third heart sound S3 on the processed HS signal; and
calculating the at least first normalized and second unnormalized signal metrics includes calculating two or more of a first time interval indicative of the pre-ejection period (PEP), a second time interval indicative of the left ventricular ejection time (LVET), or a ratio between the first and second time intervals, the first time interval including an interval between the R wave and the S1 heart sound, the second time interval including an interval between the S1 and S2 heart sounds.

* * * * *